United States Patent [19]

Numata et al.

[11] Patent Number: 4,837,345
[45] Date of Patent: Jun. 6, 1989

[54] PROCESS FOR THE PRODUCTION OF TETRAHYDROPYRAN-3-ONE DERIVATIVES

[75] Inventors: Tatsuo Numata; Masataka Hatanaka; Junichi Watanabe, all of Funabashi, Japan

[73] Assignee: Nissan Chemical Industries Ltd., Tokyo, Japan

[21] Appl. No.: 140,211

[22] Filed: Dec. 31, 1987

[30] Foreign Application Priority Data

Jan. 9, 1987 [JP] Japan ................... 62-3026

[51] Int. Cl.$^4$ ........................... C07D 309/30
[52] U.S. Cl. ................. 549/416; 549/419; 549/420; 549/423
[58] Field of Search ............... 549/416, 419, 420, 423

[56] References Cited

FOREIGN PATENT DOCUMENTS 53-9772 1/1978 Japan .

*Primary Examiner*—Nicky Chan
*Attorney, Agent, or Firm*—Oblon, Spivak, McClelland, Maier & Neustadt

[57] ABSTRACT

A process for producing a tetrahydropyran-3-one derivative of the formula:

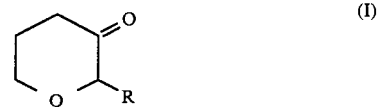

(I)

wherein R is a hydrogen atom; a straight chained or branched $C_1$–$C_{10}$ alkyl group which is unsubstituted or substituted by a halogen atom, a hydroxyl group, a $C_1$–$C_6$ alkoxy group, a $C_1$–$C_6$ alkylthio group, a $C_1$–$C_6$ alkylcarbonyloxy group, a $C_1$–$C_6$ alkoxycarbonyl group, a $C_1$–$C_6$ mono- or dialkylamino group, a $C_3$–$C_6$ cycloaklyl group, a $C_1$–$C_6$ alkylaminocarbonyl group, a $C_1$–$C_6$ alkylcarbonylamino group, a $C_1$–$C_6$ alkylcarbonyl group or a phenyl or benzoyl group which is unsubstituted or substituted by a halogen atom, a $C_1$–$C_6$ alkyl group, a $C_1$–$C_6$ alkoxy group, a $C_1$–$C_6$ alkythio group or a $C_1$–$C_6$ alkoxycarbonyl group; a $C_3$–$C_6$ cycloalkyl group; or a phenyl or biphenyl group which is unsubstituted or substituted by a halogen atom, a $C_1$–$C_6$ alkoxy group or $C_1$–$C_6$ alkylthio group, which comprises reacting a 2H-pyran-3(6H)-one derivative of the formula:

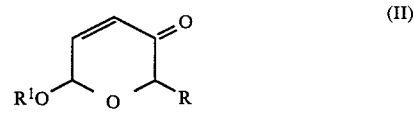

(II)

wherein R is as defined above, and R' is a straight chained or branched $C_1$–$C_6$ acyl group which is unsubstituted or substituted by a halogen atom; a benzoyl group; a $C_1$–$C_6$ alkoxycarbonyl group; or a mono- or dialkylaminocarbonyl group which is unsubstituted or substituted by a $C_1$–$C_3$ alkyl group or a phenyl group, with hydrogen in the presence of a catalyst selected from the group consisting of cobalt, nickel, ruthenium, rhodium, palladium, iridium, platinum and copper chromite.

5 Claims, No Drawings

PROCESS FOR THE PRODUCTION OF TETRAHYDROPYRAN-3-ONE DERIVATIVES

BACKGROUND OF THE INVENTION

Field of the Invention

The present invention relates to a novel process for producing tetrahydropyran-3-one derivatives of the formula:

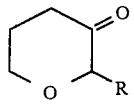

(I)

wherein R is a hydrogen atom; a straight chained or branched $C_1$–$C_{10}$ alkyl group which is unsubstituted or substituted by a halogen atom, a hydroxyl group, a $C_1$–$C_6$ alkoxy group, a $C_1$–$C_6$ alkythio group, a $C_1$–$C_6$ alkylcarbonyloxy group, a $C_1$–$C_6$ alkoxycarbonyl group, a $C_1$–$C_6$ mono- or dialkylamino group, a $C_3$–$C_6$ cycloalkyl group, a $C_1$–$C_6$ alkylaminocarbonyl group, a $C_1$–$C_6$ alkylcarbonylamino group, a $C_1$–$C_6$ alkylcarbonyl group or a phenyl or benzoyl group which is unsubstituted or substituted by a halogen atom, a $C_1$–$C_6$ alkyl group, a $C_1$–$C_6$ alkoxy group, a $C_1$–$C_6$ akylthio group or a $C_1$–$C_6$ alkoxycarbonyl group; a $C_3$–$C_6$ cycloalkyl group; or a phenyl or biphenyl group which is unsubstituted or substituted by a halogen atom, a $C_1$–$C_6$ alkoxy group or $C_1$–$C_6$ alkylthio group.

DISCUSSION OF BACKGROUND

The tetrahydropyran-3-one derivatives of the formula I are useful as intermediates for perfumes, medicines and agricultural chemicals. For example, they are useful as intermediates for 2-(2-imidazolin-2-yl)pyridine-3-carboxylic aid type herbicides disclosed in U.S. Pat. No. 4,696,694.

Heretofore, for the production of the tetrahydropyran-3-one derivatives of the formula I, there have been known a method of oxidizing tetrahydropyran-3-ols as disclosed in the Journal of Organic Chemistry, 43, 4106 (1978) and a method of thermally decomposing trans-2-ethoxy-3-hydroxytetrahydropyrans as disclosed in Chemische Berichte, 94, 1860 (1961).

However, such conventional methods require starting materials which are hardly available or require reactions under severe conditions. Thus, they are not economical methods capable of producing the tetrahydropyran-3-one derivatives of the formula I readily and in good yield.

SUMMARY OF THE INVENTION

In view of the drawbacks of the conventional methods, the present inventors have conducted extensive research for a process for producing the tetrahydropyran-3-one derivatives of the formula I under mild reaction conditions from inexpensive and readily available starting materials and, as a result, have found it possible to readily attain the above object by using as the starting material 2H-pyran-3(6H)-one derivatives of the formula II which can readily be obtained from furfural or furfuryl alcohols. The present invention has been accomplished on the basis of this discovery.

Thus, the present invention provides a process for producing a tetrahydropyran-3-one derivative of the formula:

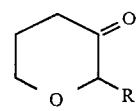

(I)

wherein R is a hydrogen atom; a straight chained or branched $C_1$–$C_{10}$ alkyl group which is unsubstituted or substituted by a halogen atom, a hydroxyl group, a $C_1$–$C_6$ alkoxy group, a $C_1$–$C_6$ alkylthio group, a $C_1$–$C_6$ alkylcarbonyloxy group, a $C_1$–$C_6$ alkoxycarbonyl group, a $C_1$–$C_6$ mono- or dialkylamino group, a $C_3$–$C_6$ cycloalkyl group, a $C_1$–$C_6$ alkylaminocarbonyl group, a $C_1$–$C_6$ alkylcarbonylamino group, a $C_1$–$C_6$ alkylcarbonyl group or a phenyl or benzoyl group which is unsubstituted or substituted by a halogen atom, a $C_1$–$C_6$ alkyl group, a $C_1$–$C_6$ alkoxy group, a $C_1$–$C_6$ alkylthio group or a $C_1$–$C_6$ alkoxycarbonyl group; a $C_3$–$C_6$ cycloalkyl group; or a phenyl or biphenyl group which is unsubstituted or substituted by a halogen atom, a $C_1$–$C_6$ alkoxy group or $C_1$–$C_6$ alkylthio group, which comprises reacting a 2H-pyran-3(6H)-one derivative of the formula:

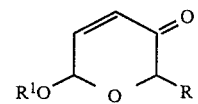

(II)

wherein R is as defined above, and $R^1$ is a straight chained or branched $C_1$–$C_6$ acyl group which is unsubstituted or substituted by a halogen atom; a benzoyl group; a $C_1$–$C_6$ alkoxycarbonyl group; or a mono- or dialkylaminocarbonyl group which is unsubstituted or substituted by a $C_1$–$C_3$ alkyl group or a phenyl group, with hydrogen in the presence of a catalyst selected from the group consisting of cobalt, nickel, ruthenium, rhodium, palladium, iridium, platinum and copper chromite.

DETAILED DESCRIPTION OF THE PREFERRED EMBODIMENTS

In the present invention, the compound of the formula II is reacted with hydrogen in the presence of a catalyst to conduct the hydrogenation of the double bond and the hydrogenolysis to remove the $R^1O$ group, to obtain the compound of the formula I.

As the catalyst, various usual catalysts such as cobalt, nickel, ruthenium, rhodium, palladium, iridium, platinum and copper-chromite may be employed. It is also possible to use a catalyst supported on a carrier such as carbon or active alumina.

In the present invention, it is particularly preferred to use palladium and platinum catalyst.

The catalyst is used preferably in an amount within a range of from 0.0005 to 1.0 parts by weight, more preferably from 0.01 to 0.10 as the metal or compound relative to the weight of the compound of the formula II.

There is no particular restriction as to the reaction pressure. However, it is preferably within a range of from atmospheric pressure to 200 kg/cm². The reaction usually proceeds adequately even under atmospheric pressure.

There is no particular restriction as to the reaction temperature. However, it is preferably within a range of from 10° to 100° C.

The reaction may be conducted in the absence of a solvent. However, it is preferred to employ a solvent. Such a solvent may be water, an alcohol such as methanol or ethanol, an ether such as diethyl ether, diisopropyl ether, 1,2-dimethoxyethane, dioxane or tetrahydrofuran, a halogenated hydrocarbon such as methylene chloride, chloroform or carbontetrachloride, an aliphatic hydrocarbon such as n-hexane or cyclohexane, an ester such as methyl acetate or ethyl acetate, a ketone such as aceton or methyl ethyl ketone, an aromatic hydrocarbon such as benzene, toluene or xylene, a carboxylic acid such as acetic acid, or an amide such as dimethyl acetomaide or N-methylpyrrolidone. If necessary, the above solvents may be employed in the form of a solvent mixture.

In the present invention, the reaction may be conducted, if necessary, with an addition of an organic base such as pyridine.

Under the above-mentioned reaction conditions, the hydrogenation of the double bond and the hydrogenolysis to remove the $R^1O$ group proceed smoothly.

The compound of the formula II is a known compound and may be prepared, for example, by the following scheme.

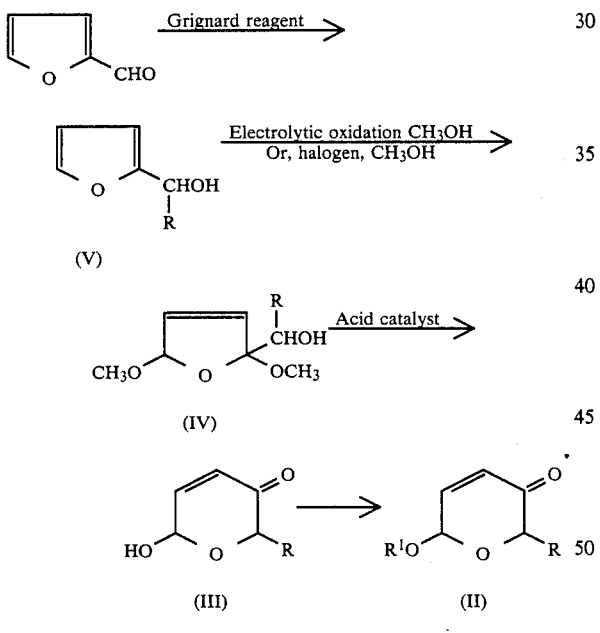

wherein R and $R^1$ are as defined above.

Namely, a compound of the formula V can be prepared by reacting furfural with a suitable Grignard reagent in accordance with e.g. the method disclosed in Chemical Abstracts, 44 and 1092d (1950).

A compound of the formula IV can be prepared from the compound of the formula V in accordance with e.g. the method disclosed in the Acta Chem. Scand., 2, 109 (1948), Acta Chem. Scand., 9, 17 (1955), Ann., 516, 231 (1935), or U.S. Pat. No. 2,714,576 or 4,342,697.

Then, a compound of the formula III can be prepared from the compound of the formula IV, and a compound of the formula II can be prepared from the compound of the formula III, in accordance with e.g. the methods disclosed in Tetrahedron, 27, 1973 (1971), Tetrahedron Letters, 17, 1363 (1976), and Chemistry Letters, 495 (1976).

According to the present invention, the compounds of the formula I can be prepared in good yield under mild conditions from inexpensive and readily available starting materials.

Now, the present invention will be described in further detail with reference to Examples and Reference Examples. However, it should be understood that the present invention is by no means restricted by such specific Examples.

REFERENCE EXAMPLE 1

Preparation of 6-acetoxy-2H-pyran-3(6H)-one 24.0 g of 6-hydroxy-2H-pyran-3(6H)-one was dissolved in 80 ml of acetic anhydride. After cooling the solution to 0° C., 30 ml of pyridine was dropwise added thereto.

The mixture was stirred for 3 hours, and then the solvent was distilled off under reduced pressure. The residue was purified by column chromatography, and further subjected to distillation under reduced pressure to obtain 24.3 g (yield: 74%) of the above-identified compound.

Boiling point: 68°–87° C. (0.15 mmHg)

PMR (ppm. $\delta(CDCl_3)$). 2.10(s, 3H), 4.11(d, J=17Hz, 1H), 4.15(d, J=17Hz, 1H), 6.28(d, J=10Hz, 1H), 6.41(d, J=3Hz, 1H), 6.88(dd, J=10Hz, 3Hz, 1H).

In the same manner as above, the following compounds can be prepared:
6-acetoxy-2-methyl-2H-pyran-3(6H)-one,
6-acetoxy-2-ethyl-2H-pyran-3(6H)-one,
6-acetoxy-2-propyl-2H-pyran-3(6H)-one,
6-acetoxy-2-isopropyl-2H-pyran-3(6H)-one,
6-acetoxy-2-n-butyl-2H-pyran-3(6H)-one,
6-acetoxy-2-n-pentyl-2H-pyran-3(6H)-one,
6-acetoxy-2-n-hexyl-2H-pyran-3(6H)-one,
6-acetoxy-2-n-heptyl-2H-pyran-3(6H)-one,
6-acetoxy-2-n-octyl-2H-pyran-3(6H)-one,
6-acetoxy-2-n-nonyl-2H-pyran-3(6H)-one,
6-acetoxy-2-n-decyl-2H-pyran-3(6H)-one,
6-acetoxy-2-cyclohexyl-2H-pyran-3(6H)-one,
6-acetoxy-2-phenyl-2H-pyran-3(6H)-one,
6-acetoxy-2-benzyl-2H-pyran-3(6H)-one,
6-acetoxy-2-biphenyl-2H-pyran-3(6H)-one,
6-trifluoroacetoxy-2-H-pyran-3(6H)-one,
6-acetoxy-2-hydroxymethyl-2H-pyran-3(6H)-one, and
6-acetoxy-2-acetoxymethyl-2H-pyran-3(6H)-one.

REFERENCE EXAMPLE 2

Preparation of 6-methoxycarbonyloxy-2H-pyran-3(6H)-one 12 g of 6-hydroxy-2H-pyran-3(6H)-one was dissolved in 100 ml of methylene chloride, and the solution was cooled to 0° C. Then, 9.4 g of methyl chlorocarbonate was added thereto, and a solution comprising 10.6 g of triethylamine and 20 ml of methylene chloride was dropwise added thereto. The mixture was stirred for 3 hours, and the reaction mixture was poured into ice water and extracted with methylene chloride. The solvent was distilled off under reduced pressure, and the residue was subjected to distillation under reduced pressure to obtain 10.3 g (yield: 60%) of the above-identified compound.

PMR (ppm. $\delta(CDCl_3)$). 3.70(s, 3H), 4.14(d, J=17Hz, 1H), 4.55(d, J=17Hz, 1H), 6.22(d, J=10Hz, 1H), 6.33(d, J=3Hz, 1H), 6.90(dd, J=10Hz, 3Hz, 1H).

REFERENCE EXAMPLE 3

Preparation of 6-ethoxycarbonyloxy-2H-pyran-3(6H)-one 12 g of 6-hydroxy-2H-pyran-3(6H)-one was dissolved in 100 ml of methylene chloride, and the solution was cooled to 0° C. Then, 11.4 g of ethyl chlorocarbonate was added, and a solution comprising 10.6 g of triethylamine and 20 ml of methylene chloride was dropwise added thereto. The mixture was stirred for 3 hours, and the reaction mixture was poured into ice water and extracted with methylene chloride. The solvent was distilled off under reduced pressure, and the residue was subjected to distillation under reduced pressure to obtain 12.3 g (yield: 63%) of the above-identified compound.

Boiling point: 72°–105° C. (0.4 mmHg PMR (ppm. $\delta(CDCl_3)$) 1.33(t, J=7Hz, 3H), 4.27(q, J=7Hz, 2H), 4.14(d, J=17Hz, 1H), 4.55(d, J=17Hz, 1H), 6.20(d, J=10Hz, 1H), 6.31(d, J=3Hz, 1H), 6.88(dd, J=10Hz, 3Hz, 1H).

In the same manner as above, the following compounds can be prepared:
6-methoxycarbonyloxy-2-methyl-2H-pyran-3(6H)-one,
6-methoxycarbonyloxy-2-ethyl-2H-pyran-3(6H)-one,
6-methoxycarbonyloxy-2-phenyl-2H-pyran-3(6H)-one,
6-methoxycarbonyloxy-2-benzyl-2H-pyran-3(6H)-one,
6-ethoxycarbonyloxy-2-methyl-2H-pyran-3(6H)-one,
6-ethoxycarbonyloxy-2-ethyl-2H-pyran-3(6H)-one,
6-ethoxycarbonyloxy-2-phenyl-2H-pyran-3-(6H)-one,
6-ethoxycarbonyloxy-2-benzyl-2H-pyran-3(6H)-one,
6-butanoyloxy-2-methyl-2H-pyran-3(6H)-one,
6-n-heptanoyloxy-2H-pyran-3(6H)-one,
6-chloroacetoxy-2H-pyran-3(6H)-one,
6-(N-methylcarbamoyloxy)-2H-pyran-3(6H)-one,
6-(N,N-dimethylcarbamoyloxy)-2-methyl-2H-pyran-3(6H)-one,
6-(N-phenylcarbamoyloxy)-2H-pyran-3(6H)-one,
6-(2-methylpropanoyloxy)-2-methyl-2H-pyran-3-(6H)-one,
6-benzoyloxy-2-ethyl-2H-pyran-3(6H)-one,
6-chloroacyloxy-2-ethyl-2H-pyran-3(6H)-one,
6-(3-methylbutanoyloxy)-2-ethyl-2H-pyran-3(6H)-one

EXAMPLE 1

1.0 g of 5% palladium carbon (K-type, manufactured by Nippon Engelhard Company) was added to a solution comprising 25 g of 6-acetoxy-2H-pyran-3(6H)-one, 300 ml of tetrahydrofuran and 10 ml of water. Hydrogen was introduced at room temperature under atmospheric pressure, and the mixture was stirred. When the stirring was continued for about 120 minutes, substantially a theoretical amount of hydrogen was absorbed. After the reaction, excess hydrogen was removed, and the catalyst was separated by filtration. The solvent was distilled off from the filtrate under reduced pressure while maintaining the warm bath temperature at level of not higher than 35° C., and the residue was subjected to distillation under reduced pressure to obtain 15 g (yield: 95%) of tetrahydrofuran-3-one.

Colorless liquid, boiling point: 81°–85° C. (45 mmHg) PMR (ppm. $\delta(CDCl_3)$). 2.12(m, 2H), 2.52(t, J=6Hz, 2H), 3.84(t, J=6Hz, 2H), 3.98(s, 2H).

EXAMPLE 2

0.16 g of 5% platinum carbon manufactured by Nippon Engelhard Company was dissolved in a solution comprising 0.78 g of 6-acetoxy-2H-pyran-3(6H)-one and 25 ml of tetrahydrofuran. Hydrogen was introduced at room temperature under atmospheric pressure, and the mixture was stirred. When hydrogen was absorbed to substantially a theoretical amount, the introduction of hydrogen was stopped, and excess hydrogen was removed.

The catalyst was separated by filtration. The solvent was distilled off from the filtrate under reduced pressure while maintaining the warm bath temperature at level of not higher than 35° C., and the residue was purified by column chromatography to obtain 0.44 g (yield: 88%) of tetrahydropyran-3-one.

EXAMPLE 3

100 mg of 5% palladium carbon (K-type, manufactured by Nippon Engelhard Company) was added to a solution comprising 0.78 g of 6-methoxycarbonyloxy-2H-pyran-3(6H)-one and 30 ml of tetrahydrofuran. Hydrogen was introduced at room temperature under atmospheric pressure, and the mixture was stirred.

The stirring was continued for about 120 minutes, whereby substantially a theoretical amount of hydrogen was absorbed. After the reaction, excess hydrogen was removed, and the catalyst was separated by filtration. The solvent was distilled off from the filtrate at room temperature under reduced pressure, and then the residue was purified by column chromatography to obtain 0.45 g (yield: 100%) of tetrahydropyran-3-one.

EXAMPLE 4

100 mf of 5% palladium carbon (K-type, manufactured by Nippon Engelhard Company) was added to a solution comprising 1.86 g of 6-ethoxycarbonyloxy-2H-pyran-3(6H)-one and 60 ml of tetrahydrofuran. Hydrogen was introduced at room temperature under atmospheric pressure, and the mixture was stirred.

After the completion of the reaction, the catalyst was separated by filtration. The solvent was removed from the filtrate at room temperature under reduced pressure, and the residue was purified by column chromatography to obtain 0.83 g (yield: 83%) of tetrahydropyran-3-one.

EXAMPLES 5 to 23

Other experimental results are shown in Tables 1 and 2. In Tables 1 and 2, R and $R^1$ are the substituents of the formula II.

TABLE 1

| Example No. | $R^1$ | R | Catalyst (g) | Solvent (ml) (additive g) | Pressure | Temp. (°C.) | Yield (%) |
|---|---|---|---|---|---|---|---|
| 5 | Ac (3.12) | H | 5% Pd/C[1] (0.3) | THF(100) (Py 1.9) | Atmospheric pressure | Room temp. | 64.5 |
| 6 | Ac (15.6) | H | 5% Pd/C[1] (3.0) | THF(500) | Atmospheric pressure | Room temp. | 63 |
| 7 | Ac (0.78) | H | 5% Pd/C[1] (0.16) | MEK(25) | Atmospheric | Room temp. | 44 |

TABLE 1-continued

| Example No. | R¹ (g) | R | Catalyst (g) | Solvent (ml) (additive g) | Pressure | Temp. (°C.) | Yield (%) |
|---|---|---|---|---|---|---|---|
| 8 | Ac (0.78) | H | 5% Pd/C[1] (0.16) | (iPr)₂O (25) | Atmospheric pressure | Room temp. | 73 |
| 9 | Ac (0.78) | H | 5% Pd/C[1] (0.16) | DME (25) | Atmospheric pressure | Room temp. | 45.5 |
| 10 | Ac (0.78) | H | 5% Pd/C[1] (0.16) | Dioxane (25) | Atmospheric pressure | Room temp. | 51 |
| 11 | Ac (0.78) | H | 5% Pd/C[1] (0.16) | AcOEt (25) | Atmospheric pressure | Room temp. | 26 |
| 12 | Ac (0.78) | H | 5% Pd/C[1] (0.16) | MeOH (25) | Atmospheric pressure | Room temp. | 50.3 |
| 13 | Ac (0.78) | H | 5% Pd/C[1] (0.16) | n-Hexane (25) | Atmospheric pressure | Room temp. | 91 |
| 14 | Ac (0.78) | H | 5% Pd/C[1] (0.16) | Benzene (25) | Atmospheric pressure | Room temp. | 30 |
| 15 | Ac (0.78) | H | 5% Pd/C[1] (0.16) | THF(13) H₂O(13) | Atmospheric pressure | Room temp. | 94 |
| 16 | Ac (2.34) | H | 5% Pd/C[1] (0.12) | tBuOH(10) H₂(10) | Atmospheric pressure | Room temp. | 87 |
| 17 | Ac (3.16) | H | 5% Pd/C[1] (0.2) | H₂O(30) | Atmospheric pressure | Room temp. | 92 |
| 18 | Ac (0.78) | H | 5% Pd/C[1] (0.1) | AcOH(30) | Atmospheric pressure | Room temp. | 35 |
| 19 | MeOCO (0.86) | H | 5% Pd/C[1] (0.1) | THF(30) H₂O(3) | Atmospheric pressure | Room temp. | 83 |

Ac: acetyl group, Me: methyl group, Et: ethyl group,
iPr: isopropyl group, tBu: tertiary butyl group,
Py: pyridine, THF: tetrahydrofuran,
MEK: methyl ethyl ketone, DME: 1,2-dimethoxy ethane,
[1]5% palladium carbon (K-type) catalyst manufactured by Nippon Engelhard Company.

TABLE 2

| Example No. | R¹ (g) | R | Catalyst (g) | Solvent (ml) (additive g) | Pressure | Temp. (°C.) | Yield (%) |
|---|---|---|---|---|---|---|---|
| 20 | Ac (0.78) | H | 10% Pd/C[2] (0.1) | THF(30) | 30 kg/cm²G | 150 | 32 |
| 21 | Ac (1.56) | H | 10% Pd/C[2] (0.1) | THF(50) | Atmospheric pressure | Room temp. | 27.7 |
| 22 | Ac (0.78) | H | 10% Pd/C[2] (0.1) | THF(25) (Py 0.4) | Atmospheric pressure | Room temp. | 80 |
| 23 | Ac (1.56) | H | PtO₂[3] (0.1) | THF(50) | Atmospheric pressure | Room temp. | 40 |

Ac: acetyl group, Pr: pyridine, THF: tetrahydrofuran,
[2]10% palladium carbon catalyst manufactured by Kawaken fine chemical
[3]Platinum oxide catalyst manufactured by Wako Junyaku

What is claimed is:

1. A process for producing a tetrahydropyran-3-one derivative of the formula I:

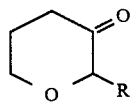

wherein R is a hydrogen atom; a straight-chained or branched $C_1$–$C_{10}$ alkyl group which is unsubstituted or substituted by a halogen atom, a hydroxyl group, a $C_1$–$C_6$ alkoxy group, a $C_1$–$C_6$ alkylthio group, a $C_1$–$C_6$ alkylcarbonyloxy group, a $C_1$–$C_6$ alkoxycarbonyl group, a $C_1$–$C_6$ mono- or dialkylamino group, a $C_3$–$C_6$ cycloalkyl group, a $C_1$–$C_6$ alkylaminocarbonyl group, a $C_1$–$C_6$ alkylcarbonylamino group, a $C_1$–$C_6$ alkylcarbonyl group or a phenyl or benzyl group which is unsubstituted or substituted by a halogen atom, a $C_1$–$C_6$ alkyl group, a $C_1$–$C_6$ alkoxy group, a $C_1$–$C_6$ alkylthio group or a $C_1$–$C_6$ alkoxycarbonyl group; a $C_3$–$C_6$ cycloalkyl group; or a phenyl or biphenyl group which is unsubstituted or substituted by a halogen atom, a $C_1$–$C_6$ alkoxy group or $C_1$–$C_6$ alkylthio group, which consists essentially of reacting a 2H-pyran-3(6H)-one derivative of the formula II:

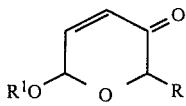

II wherein R is as defined above, and R₁ is an acetyl group, with hydrogen in an aqueous organic medium comprising water and tetrahydrofuran or A-butyl alcohol in the presence of a palladium catalyst.

2. The process according to claim 1, wherein the reaction is conducted at a pressure of from atmospheric pressure to 200 kg/cm².

3. The process according to claim 1, wherein the reaction is conducted at a temperature of from 10° to 100° C.

4. The process according to claim 1, wherein said palladium catalyst is used in an amount of about 0.0005 to 1.0 parts by weight relative to the weight of the compound of the formula II used.

5. The process according to claim 4, wherein about 0.01 to 0.10 parts by weight of the palladium catalyst is used relative to the weight of the compound of the formula II used.

* * * * *